(12) United States Patent
Merrell et al.

(10) Patent No.: US 10,525,223 B2
(45) Date of Patent: Jan. 7, 2020

(54) BAG-VALVE-MASK

(71) Applicant: COMPACT MEDICAL SOLUTIONS LLC, Indianapolis, IN (US)

(72) Inventors: Jonathan Merrell, Indianapolis, IN (US); Adam Scott, Anderson, IN (US); Dillan Nayee, Fishers, IN (US); Varun Prakash, Naperville, IL (US)

(73) Assignee: COMPACT MEDICAL SOLUTIONS, LLC, Indianapolis, IN (US)

( * ) Notice: Subject to any disclaimer, the term of this patent is extended or adjusted under 35 U.S.C. 154(b) by 254 days.

(21) Appl. No.: 15/488,241

(22) Filed: Apr. 14, 2017

(65) Prior Publication Data

US 2018/0296788 A1    Oct. 18, 2018

(51) Int. Cl.
*A61M 16/08* (2006.01)
*A61M 16/00* (2006.01)
*A61M 16/06* (2006.01)
*A61M 16/10* (2006.01)
*A61M 16/20* (2006.01)

(52) U.S. Cl.
CPC .... *A61M 16/0883* (2014.02); *A61M 16/0078* (2013.01); *A61M 16/0084* (2014.02); *A61M 16/0622* (2014.02); *A61M 16/0816* (2013.01); *A61M 16/105* (2013.01); *A61M 16/20* (2013.01); *A61M 16/208* (2013.01); *A61M 16/209* (2014.02)

(58) Field of Classification Search
CPC .......... A61M 16/0084; A61M 16/0078; A61M 16/0622; A61M 16/0883; A61M 16/0816; A61M 16/00; A61M 16/06; A61M 16/08; A62B 25/00; A62B 25/005
See application file for complete search history.

(56) References Cited

U.S. PATENT DOCUMENTS

| 3,063,620 | A * | 11/1962 | Black ............... A61M 16/0078 |
| | | | 128/205.13 |
| 2010/0236557 | A1* | 9/2010 | Reisman ........... A61M 16/0078 |
| | | | 128/205.13 |
| 2013/0192601 | A1* | 8/2013 | Reischl ................. A61M 16/06 |
| | | | 128/205.25 |
| 2016/0263339 | A1* | 9/2016 | Greenberg ........... A61M 16/06 |
| 2018/0272096 | A1* | 9/2018 | Rubin ............... A61M 16/0816 |

* cited by examiner

*Primary Examiner* — Jan Christopher L Merene
*Assistant Examiner* — Cana A Gallegos
(74) *Attorney, Agent, or Firm* — Merchant & Gould P.C.

(57) ABSTRACT

A respiratory assisting device comprising of an expandable bag which has a bilayer that can be inflated in order to give the bag a rigid and predetermined shape. The bag can then be compressed in order to displace inspiratory gas that is in the inner cavity and deliver it to the patient. The bag includes a one-way valve that passes through the bilayer allowing the inner cavity of the bag to fill with ambient air when the air within the cavity has been expended. The bag portion is connected to an air-tight hollow wall prism shape enclosure via a T-connector piece. This t-shaped connecting piece allows the air to pass through two manifold chambers that attach to another t-shaped connecting piece.

9 Claims, 13 Drawing Sheets

BAG-VALVE-MASK

BACKGROUND OF THE INVENTION

Field of the Invention

The invention relates to a bag-valve-mask or resuscitator used to ventilate patients in a field setting.

Background Art

The present invention relates to the compactness and portability of a lifesaving medical device sometimes called a resuscitator or a bag-valve-mask.

A bag-valve-mask (BVM) is a device used to temporarily push air into the lungs of a patient who is unconscious or otherwise unable to breathe on their own. These devices are found in hospitals and in ambulances throughout the country and in most developed parts of the world. A BVM is one of most fundamental pieces of lifesaving equipment.

BVMs have existed for many years. The first such device was introduced by Dean R. Wallace in 1966 (U.S. Pat. No. 3,473,529). Numerous modifications and enhancements have been made to BVMs over the years, these include enhanced 2-way valves (ex. U.S. Pat. No. 5,109,840), the addition of a high-pressure relieving "pop-off" valve (ex. U.S. Pat. No. 6,792,947), and the attachment of an oxygen reservoir to the bag to increase the percent of oxygen content of air flowing into the self-inflating bag portion of the device. Some examples of these oxygen reservoir resuscitators may be found in U.S. Pat. Nos. 4,501,271, and 4,821,713, The original invention of the bag-valve-mask with its subsequent modifications have made it possible for lifesavers to intervene on behalf of millions of patients. However, BVMs are not commonly on hand in most public and private settings. Outside of an ambulance, a hospital or similar clinical location, BVMs are not typically readily available. The principle limitation to the portability of current BVMs which is addressed by this invention is their bulk. The invention herein disclosed addresses this limitation in multiple ways.

BVMs are comprised of three key components: a self-inflating bag, a two-way valve, and a mask. The bag is designed to expand, fill and retain a volume of air. This volume constitutes the next "breath" that a patient is to receive. When the bag is compressed by a lifesaver's hand the breath is pushed through the two-way valve and down into the mask portion of the device. The mask is kept in contact with the patient's face and directs the breath downward and into the mouth or nasal passage of the victim and into their lungs. When the bag compression is released, the bag expands and a new volume of "fresh" air is drawn into the bag while the original breath of "used" air exits the patient and is released into the ambient air via the two-way valve.

Self-inflating or self-expanding bags are bulky. They typically hold over a liter of air (in an adult model) even when not in use. Two-way valves are also bulky, and prior to this invention, make use of a rigid plastic construct that is most commonly shaped in a 90-degree angle. This angle is ideal for function, but not for creating a compact device. The mask is similarly bulky and typically employs a rigid plastic triangular-shaped device with a soft rubber balloon about a perimeter that interfaces with and forms a seal around the mouth and nose of a victim. Each of these components is bulky in its own right and together, these form a device that is too large and obtuse to be carried in public by individuals who are trained to use them. Thus, when an emergency arises in most non-clinical settings, a BVM is not typically available until after an ambulance has arrived.

Efforts have been made in the past to reduce the overall space occupied by these devices. This includes an entirely collapsible bag with flexible hollow body that can be stowed into a container. An example is described in U.S. Pat. No. 8,443,803. In attempts to make the device smaller, thinner materials have been used. This results in bag-valve-masks that are suitable for one-time use, due to the device losing functionality after its use. An example is described in U.S. Pat. No. 5,163,424.

SUMMARY OF THE INVENTION

One aspect of the invention is a compact self-inflating bag whose walls are comprised not of a single layer of compressible material, but of two layers of material with an airspace in between the layers. This airspace is also referred to as the interlayer space. For descriptive purposes the term "bilayer" will be used to describe two layers of material. The airspace between the layers which form the wall of the bag, is distinct from the airspace, cavity, or plenum formed by the bilayer bag, which contains the air or breath that is expelled from the bag into the valve and mask and ultimately to the patient. This bilayer can be inflated or expanded by either inflation or by pumping air into the airspace between the layers in order to expand the bag and/or the activation of an elongate member or spring found within the bilayer or on one of the bilayers which will give the bag its shape when the bag or bias the bag when the bag is not compressed. The use of a bilayer material or biasing elongate member allows the walls of the bag to be constructed of thinner membranes and serves to minimize the bulk of the largest component of the BVM as well as maintain bag functionality over time.

The biasing elongate member or spring is to be made of a material such as metal, fiberglass, carbon fiber, plastic, or any other structural material that will bias the bag in an inflated or expanded configuration when the elongate member is incorporated on or within the bag walls. In other embodiments, the bag walls include a pressurized fluid or gas, preformed bag material, ridged structural material, or any combination of which will expand the bag for use from a stowed configuration, return to an uncompressed or biased shape when compression force is removed or collapsed for storage.

The next aspect of the invention is the unique valve body of the device. Rather than directing a breath through a two-way valve with a 90-degree angle as is common in existing BVMs, this invention channels each breath through parallel passages or manifolds formed by the hollow walls of the valve body before passing through the two-way valve and down to the patient. The valve body also includes t-shaped connector pieces to direct air from the bag to the manifolds and from the manifolds to the mask. The connector pieces are rotatable about their connections to the manifolds which permits the two expandable portions of the device (the bag and the mask) to fold into the area between the manifolds of the valve body for storage and transportation purposes. This design makes it possible for the bag and the mask of the device to be collapsed and stored within the open space between the parallel passages or manifolds of the valve body, thereby reducing the overall size of the stored device, as well as offering protection to the bag and mask when they are stored or in the storage or collapsed configuration. One skilled in the art will recognize that although the connectors are described as T-shaped, any structure or conduit that allows fluid communication between the bag and two manifolds can be used.

The valve body contains a two-way valve that is also novel and serves to greatly reduce the overall bulk of the invention. As air passes through the parallel passages or manifolds of the device, it is directed to a T-shaped connector that houses the two-way valve. Air flowing toward the patient from the compression of the bag bends or displaces a pair of leaflets, flaps or other structure found in the T-shape connector. As air is directed to the patient, the leaflets or other structure close over or otherwise obstruct bilateral vent holes in the T-shaped connector and prevent the air from escaping the device into the periphery. This ensures that the breath is transmitted downward to the patient. During exhalation when air flows from the mask to the T-shaped connector, these leaflets, flaps, diaphragms or other structures acting as a valve, return to their original position or are displaced from covering the bilateral vent holes and thus ensure that the exhaled air does not return to the bag and that it is instead directed through the bilateral vent holes and into the periphery. In an alternate embodiment, the vent holes may be occupied by diaphragms, such as duck bill diaphragms to achieve the desired valve functionality. By incorporating the components of this two-way valve into the inner walls of the valve body, this invention does not require a fixed 90-degree angle as is common for most two-way BVM valves.

Below the valve is a filter which serves as a safety mechanism to protect the patient in the event that any components from within the device were to become dislodged. The filter has a pore size to allow sufficient airflow to the patient but the pores are also small enough that the filter catches any parts of the device that may become discharged and thus prevent delivery of the dislodged parts to the patient.

The air finally flows through a collapsible mask which can be expanded when needed for use to give it a rigid shape that conforms to the patient's face for the purpose of delivering and receiving rescue breaths. The mask is made smaller or more compact by this invention. The mask is also constructed of a bilayer material and is inflatable. It can be expanded for use or collapsed for transport and storage. The inclusion of a thus-collapsible mask will make it possible to reduce the size of the stored device many times smaller than existing models of bag valve masks. The walls of the mask will therefore be lighter and thus the whole invention will be more portable than current devices.

BRIEF DESCRIPTION OF THE DRAWINGS

The invention will become more understood from the following descriptions of the above illustrations' specific orientation. Let it be noted that the invention may be viewed in different orientations other than the ones presented, and that the device is not limited to the positions shown above.

DETAILED DESCRIPTION OF THE PREFERRED EMBODIMENT

For the purpose of explanation, the terms "front", "back", "left", "right", "upper", "lower", "top", "bottom", and similar terms shall correspond to the device as positioned in the figures (above/below). The device may assume alternate orientations other than those shown. It is understood that the device characterized in the attached drawings and described thereafter are exemplary orientations of the innovative concepts defined in the claims section of this patent. Hence, the specific physical characteristics shown are not to be considered limiting unless explicitly stated. The device shown may alter in size depending on its need.

The following description relates to above figures.

Figure 1:
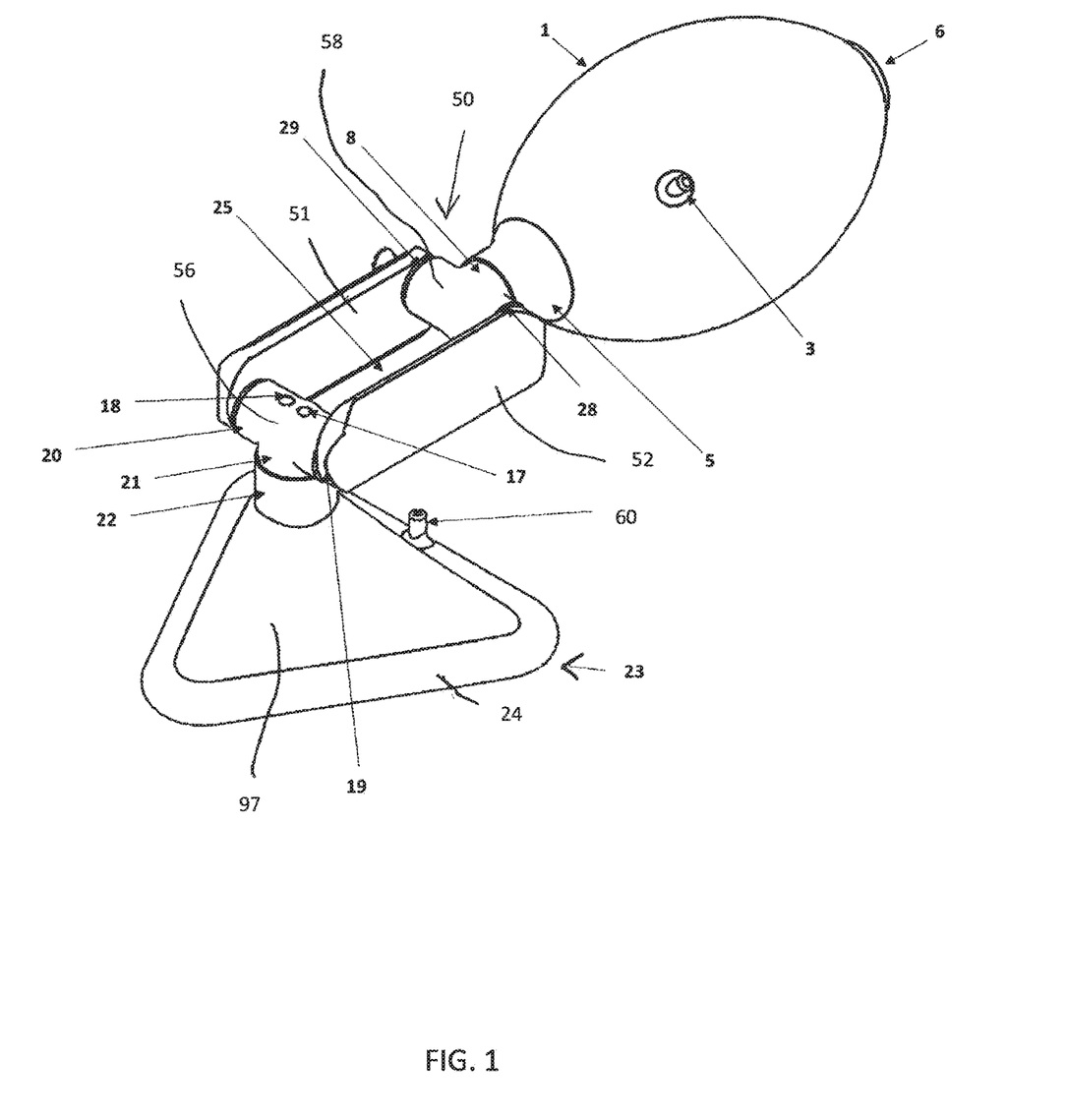
FIG. 1 is a perspective view of the entire apparatus in an unstowed or deployed configuration, with the mask and bilayer of bag inflated and the t-connectors rotated outwards so the rescuer can utilize the present invention.
Figure 2:
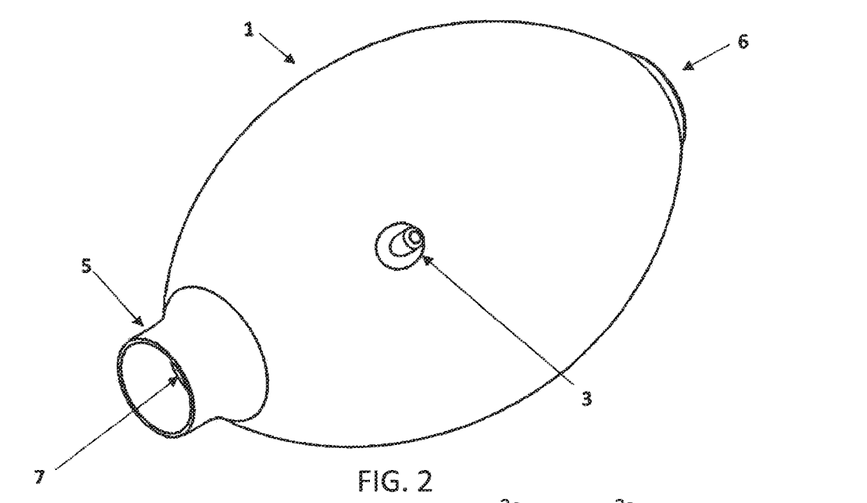
FIG. 2 is an isolated perspective view of the bag with its bilayer expanded to give it its deployed rigid shape.
Figure 3:
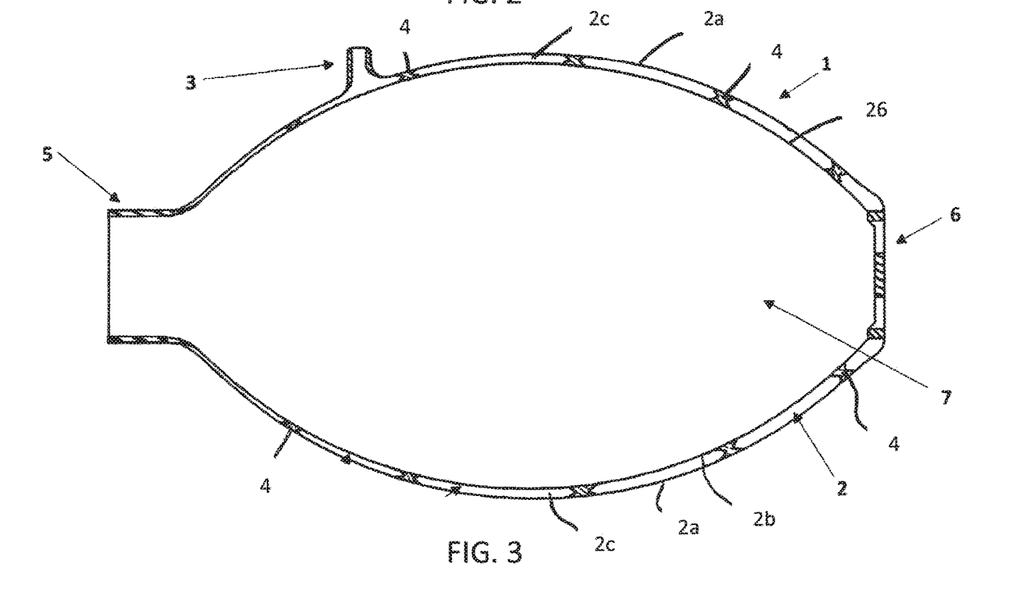
FIG. 3 is an isolated cross sectional view of the bag with its bilayer expanded to give it its deployed rigid shape, in this view one can identify both the inflatable bilayer of the bag as well as welding junctions where the two layers have been sealed together to provide stability between the two membranes of material that form the bilayer.

With reference to the Figures, the bag-valve-mask described and shown herein includes a self-inflating bag 1 as shown in FIG. 1 comprised of an inflatable (or in some other way expandable) bilayer 2, including an outer layer 2a and an inner layer 2b, as shown in FIG. 3. This inflatable bilayer 2a and 2b can be inflated or deflated as needed for product storage and transport, or use. The interlayer space or air space 2c located between the outer layer 2a and inner layer 2b can be inflated and deflated via orifice 3. (FIGS. 1, 2, 3). The inner layer 2b and the outer layer 2a are joined together at selected locations by webs 4 or other structures connecting the two layers 2a and 2b to one another, as shown in FIG. 3. One skilled in the art will recognize that the webs 4 can be placed in different locations as needed, and the placement is not limited to the specific locations shown in the figures. The webs 4 can function to maintain a predetermined distance between the inner layer 2b and outer layer 2a of the bag 1. The webs 4 help to ensure the mechanical integrity of the bag 1 as it endures high internal pressure between its two layers 2a and 2b in addition to repeated compression and re-inflation cycles during a rescue attempt.

Figure 21:
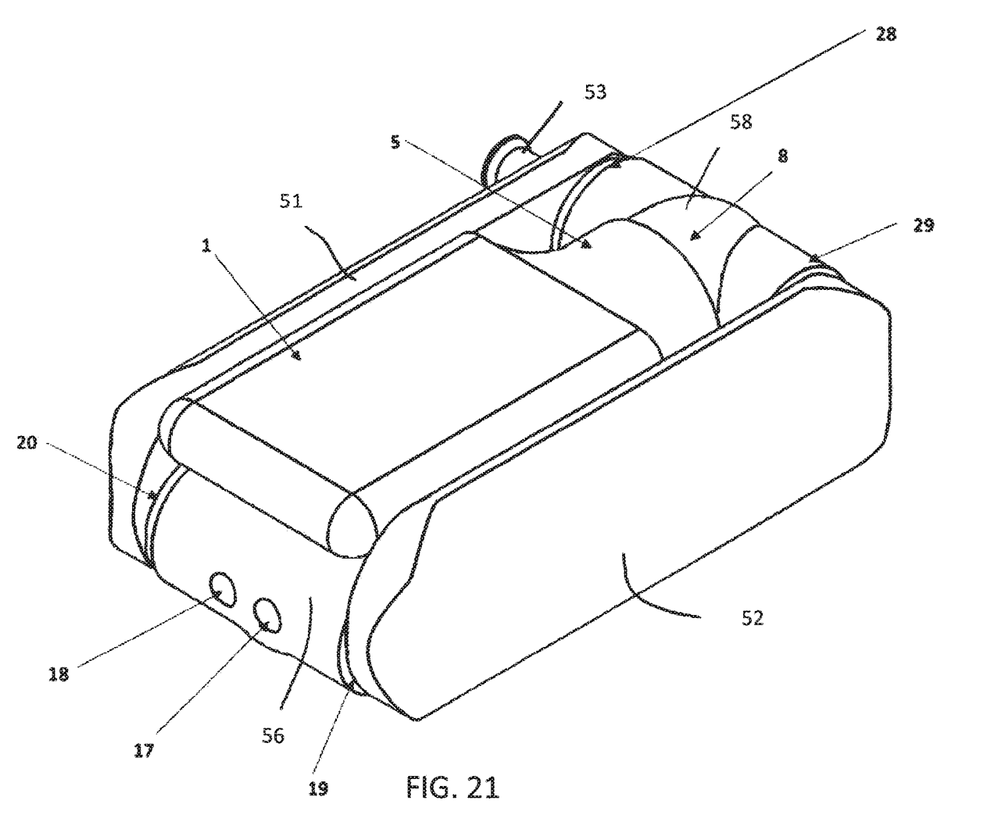
FIG. 21 is a perspective view of the entire apparatus when it is in a stowed configuration, with the mask and bilayer of bag completely collapsed for storage, and the T-connector pieces of the valve body rotated inwards so the rescuer can store or transport the present invention with ease.
Figure 22:
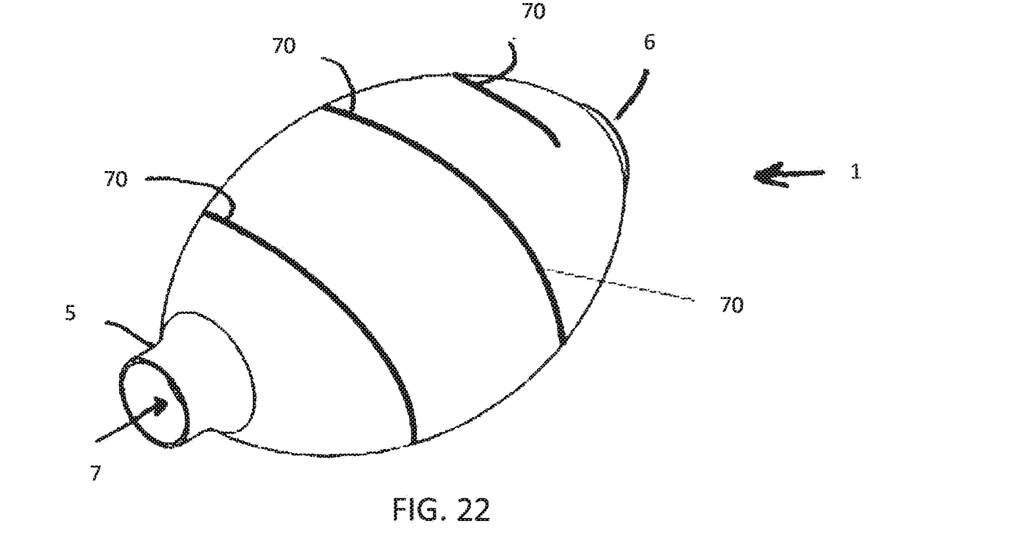
FIG. 22 is a perspective view of an alternate embodiment of the bag of the invention, the bag including a spring or biasing elongate member.
Figure 23:
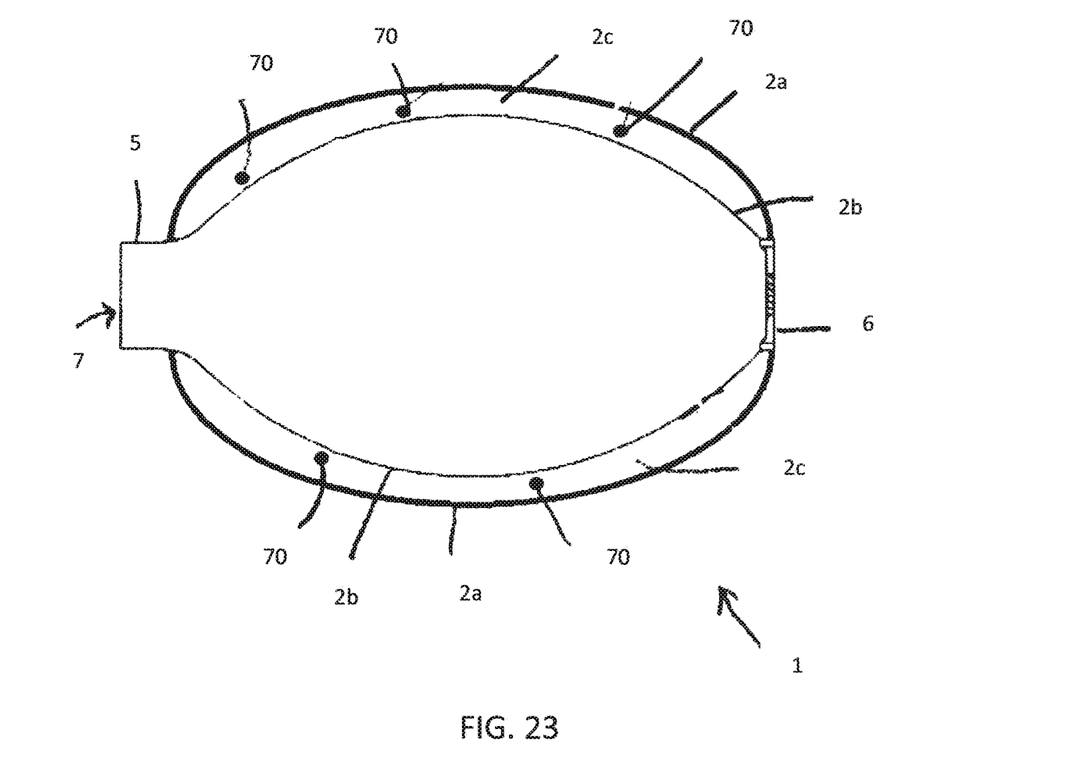
FIG. 23 is a cross-sectional view of the bag of FIG. 22.

In an alternate embodiment of the bag 1, shown in FIGS. 21 and 22, the bag 1 includes a spring or other elongate member 70. The spring or elongate member 70 is preferably located between the inner layer 2b and outer layer 2a of the bag 1, but may also be incorporated on or in either the inner layer 2b or outer layer 2a. As shown in FIGS. 21 and 22, the spring or elongate member 70 is coiled so that the bag 1 can be stowed when the spring is compressed along its axis or coiling, and deployed when the axial compression on the spring 70 is released. The spring or elongate member 70 biases the bag 1 to a predetermined shape. The coiled configuration of the spring or elongate member 70 also allows the bag 1 to be compressed and expel air when lateral or radial compression is applied, and allow the bag 1 to return to an uncompressed state when the lateral or radial pressure is removed, allowing air to enter the cavity 7 of the bag 1 as the bag uncompresses.

An orifice 3 or inflation point allows the mouth of a rescuer to be placed, form a seal, and used to inflate the airspace 2c between the two layers 2a and 2b of the bag 1. The inflation point or orifice 3 could be designed with any number of a wide array of lock-off techniques or structures in order to prevent leakage of air out of the airspace 2c. A one-way intake valve 6 is positioned on the bag and in communication with the cavity 7 or interior volume of the bag 1 to allow the cavity of the bag 7 to re-inflate after it has been compressed. The one-way intake valve 6 allows air into the cavity 7 from the periphery, but does not allow air to escape through the valve 6 under normal operating conditions.

As shown in FIGS. 1,2, and 3, the neck 5 of the bag 1 preferably includes a more rigid plastic or rubber material, as compared to the bilayer 2 of the bag 1, to enable strong attachment of the bag 1 to the connection area 8 of the T-shaped connector piece 58 of the valve body 50. In an alternate embodiment, the neck 5 of the bag 1 could be joined or formed as part of the afferent T-shaped connector piece 58. In any embodiment, the connection of the neck 5 to the connection area 8 allows for air that is expelled from cavity 7 of the bag 1 by manual compression of the bag 1 by action of a user to pass through to the middle portion of the afferent T-shaped connector piece 58 and be communicated to the valve body 50 and to the device's manifolds 51 and 52.

Figure 4:
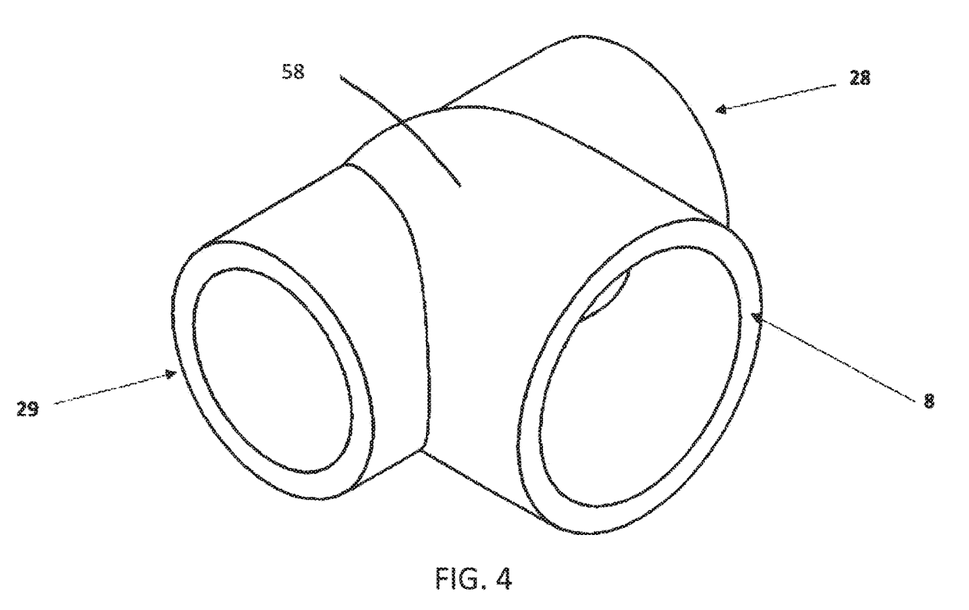
FIG. 4 is a perspective view of the T-shaped connecting piece of the valve body, that connects the two manifold air passageways to the bilayer bag shown in FIG. 2.
Figure 5:
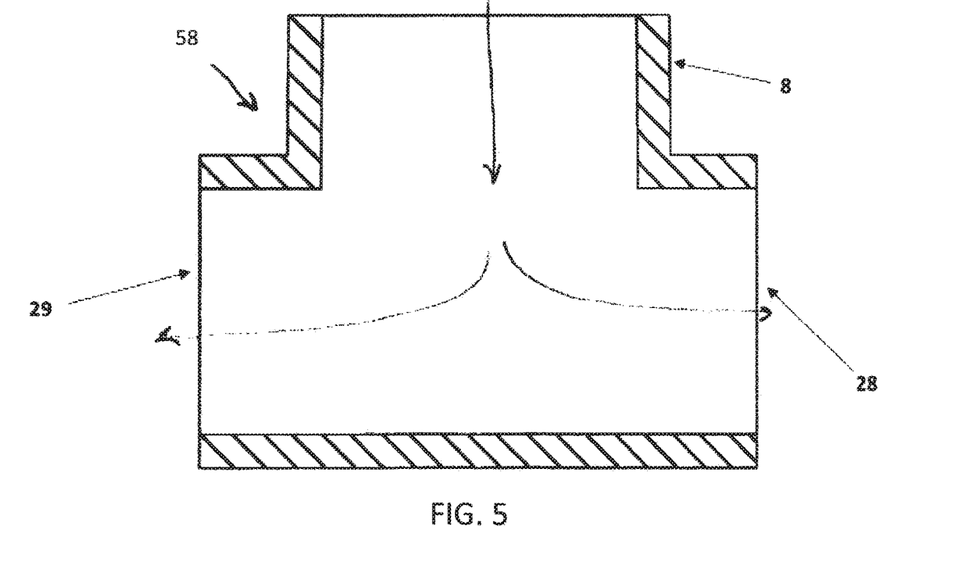
FIG. 5 is a cross-sectional view of the T-shaped connecting piece of the valve body, that connects the two manifold air passageways to the bilayer bag shown in FIG. 2.
Figure 18:
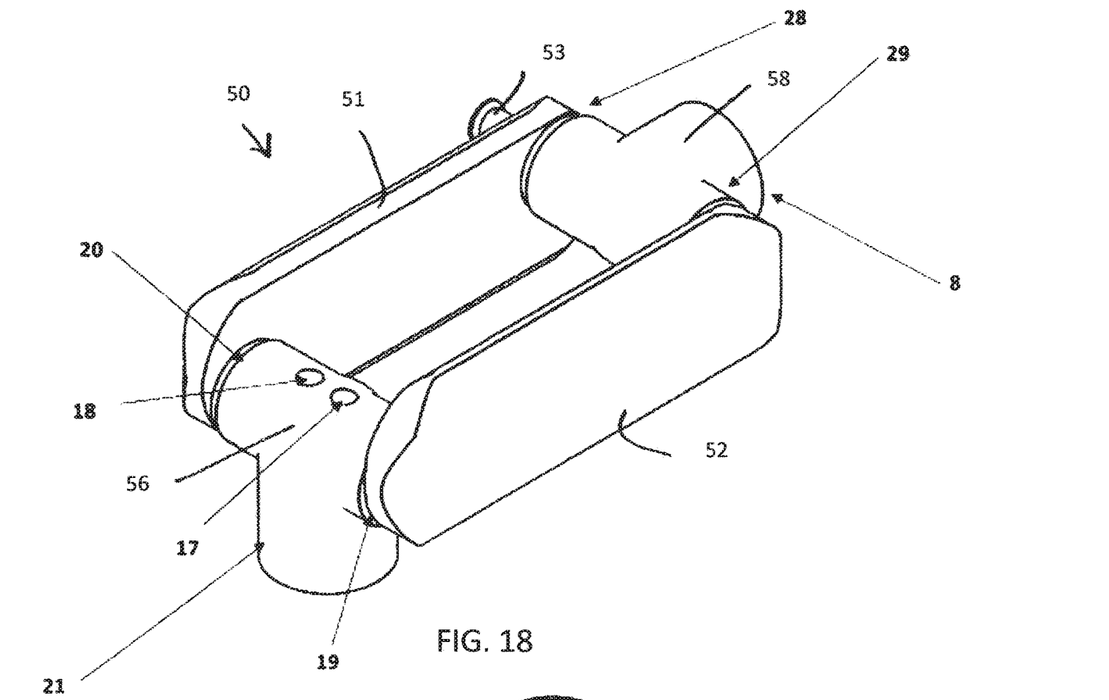
FIG. 18 is a perspective view of the open or deployed configuration of the valve body with both the mask and valve disconnected.

FIG. 18 depicts the middle portion or valve body 50 of the device and includes the two-way valve preferably located in the efferent T-Shaped connector piece 56, shown in more detail in FIGS. 13-17. Connection area 8, again, reveals the interface at which the self-inflating bag 1 is connected or joined to the afferent T-shaped connector piece 58 (FIG. 4). Air expelled from the cavity 7 of the bag 1 enters the interior or plenum of the afferent T-shaped connector piece 58 and is split in two directions to the two outflow ports 28 and 29 as it passes through the afferent T-shaped connector piece 58 into the manifolds 51 and 52 via inflow ports 9 and 10.

The valve body 50 includes manifolds 51 and 52, each manifold having a first end and a second end, each respective first end including an inflow port, and each respective second end including an outflow port. The inflow ports on each manifold are preferably in an opposing relationship so as to be connected by the afferent T-shaped connector piece 58. The outflow ports on each manifold are preferably in an opposing relationship so as to be connected by the efferent T-shaped connector piece 56. When so arranged as shown in the figures, the manifolds 51 and 52 are generally parallel and a protected space is created between the manifolds 51 and 52 and the T-shaped connector pieces 56 and 58, creating an area to store the bag 1 and mask 23.

The T-connector pieces 56 and 58 may be, attached to the manifolds 51 and 52 by means of press-fit, o-rings, threaded fit, or a snap fit, or any other way known in the art to achieve a rotatable and generally airtight fit. The T-shaped connector pieces 56 and 58 will be designed to swivel freely, but the seal will remain air-tight and resistant to disassembly by typical applied pressure or force.

FIGS. 7-10 show a pop-off valve 53 which is used as a pressure limiting means. If pressures within the air passageways 11 and 12 of the manifolds 51 and 52 exceed a predetermined value, then the pop-off valve 53 mechanism will work in a way to allow air to vent through port 13 and thus protect the lungs of the patient from barotrauma. When air pressure in the air passageway exceeds a predetermined pressure, the air pressure overcomes the bias provided by the spring 90, pushing the ball 91 past the air outlet 13 and thus allowing air to escape from the manifold 11. Once pressure is reduced, the bias of the spring 90 returns the ball 91 to a position that prevents air from escaping the air passageway 11 through the valve. Another way of accomplishing the pressure-release valve may include the use of a firm plastic membrane with a slit that releases air when internal pressures of the device are sufficiently high to push the air through the pre-formed slit. In other embodiments, other valve types or devices may be utilized to act as a pressure limiter.

Figure 6:
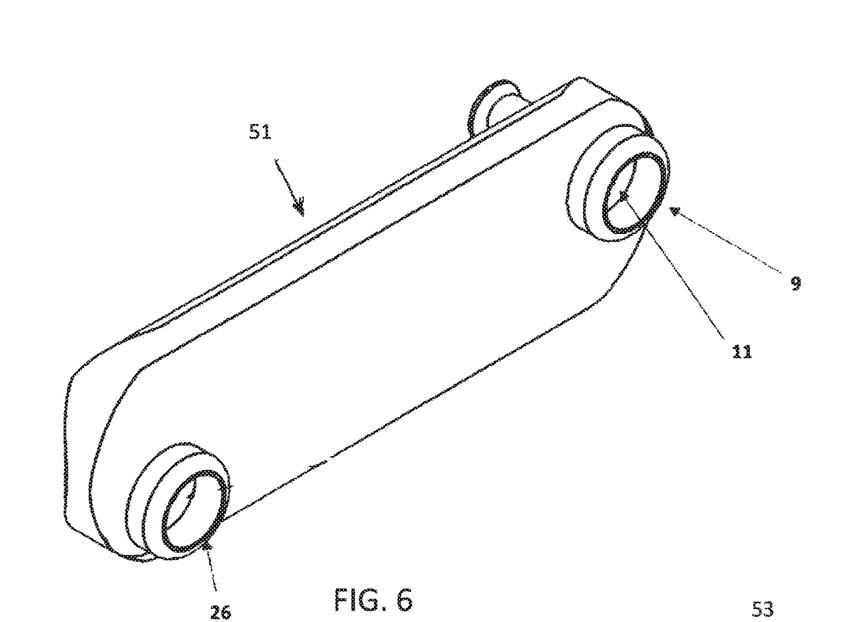
FIG. 6 is a perspective view of the left manifold piece of the valve body, in through which air flows and interacts with the pressure release valve shown in FIG. 8.
Figure 7:
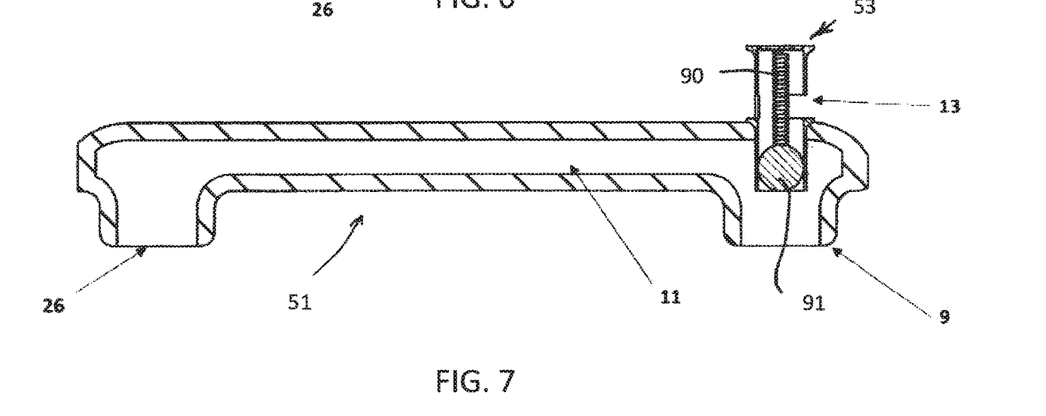
FIG. 7 is a cross-sectional view of the left manifold piece of the valve body, in through which air flows and interacts with the pressure release valve shown in FIG. 8.
Figure 8:
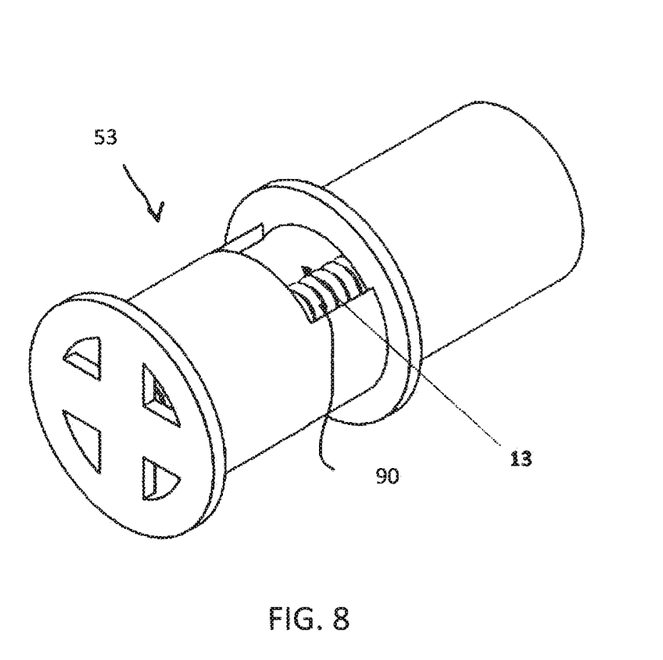
FIG. 8 is an isolated perspective view of the detached pressure-relief valve that attaches to the side of the manifold piece of the valve body.
Figure 9:
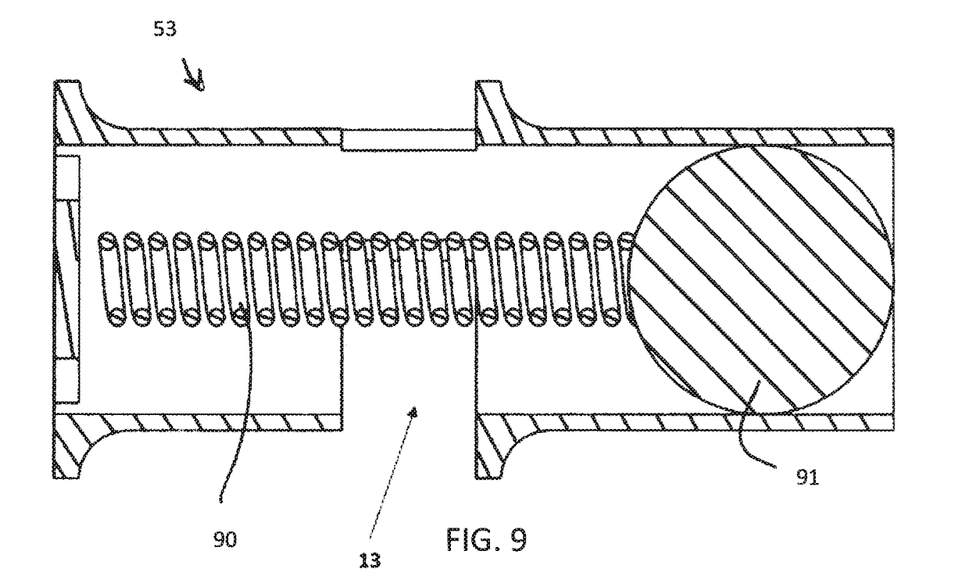
FIG. 9 is an isolated cross-sectional view of the pressure-relief valve of FIG. 8, oriented so that the air release point can be seen.
Figure 10:
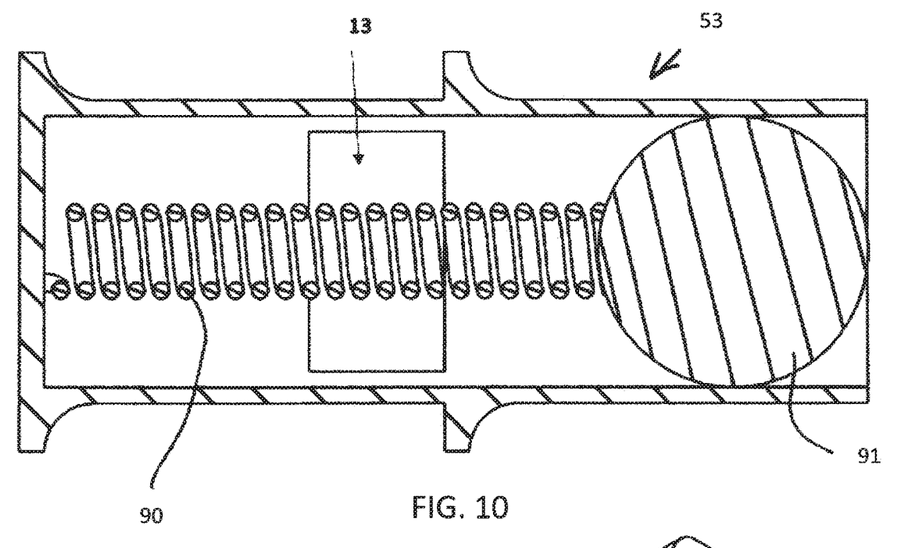
FIG. 10 is an isolated cross-sectional view of the detached pressure-relief valve of FIG. 8, oriented so that the spring connection point can be seen.
Figure 11:
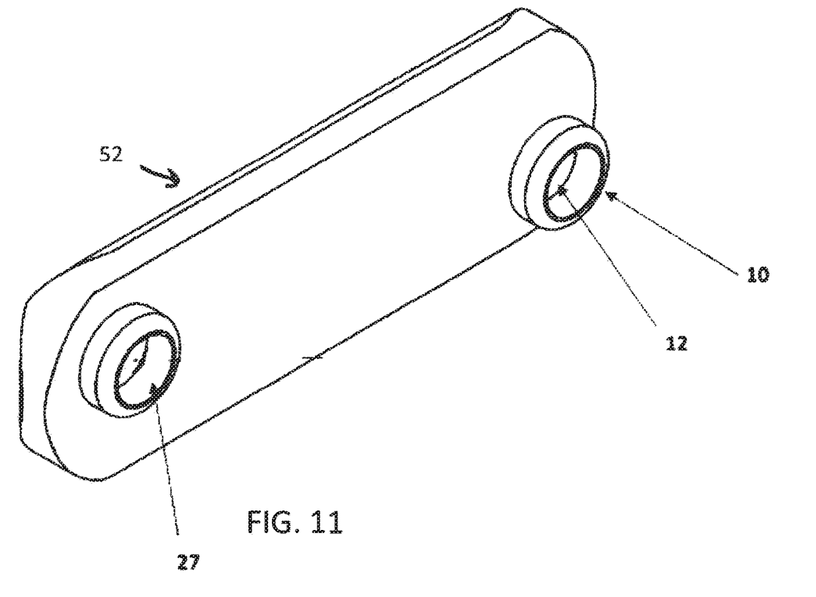
FIG. 11 is a perspective view of the right manifold piece of the valve body, through which air flows.
Figure 12:
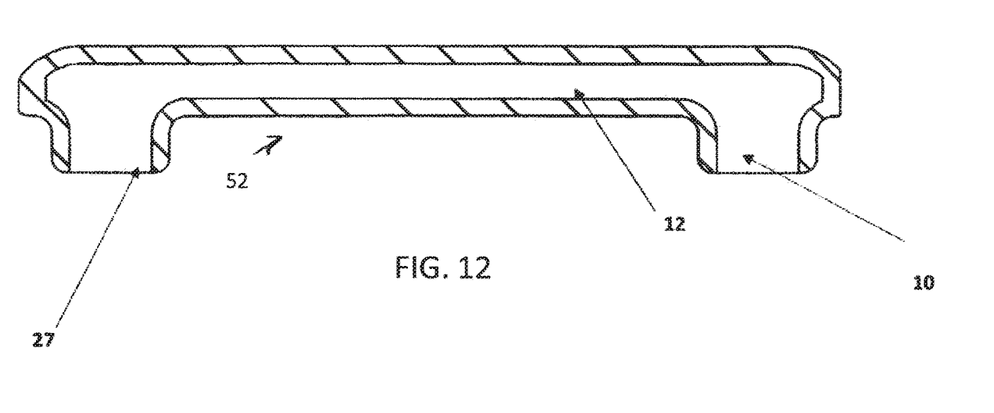
FIG. 12 is a cross-sectional view of the left manifold piece of the valve body, through which air flows.
Figure 13:
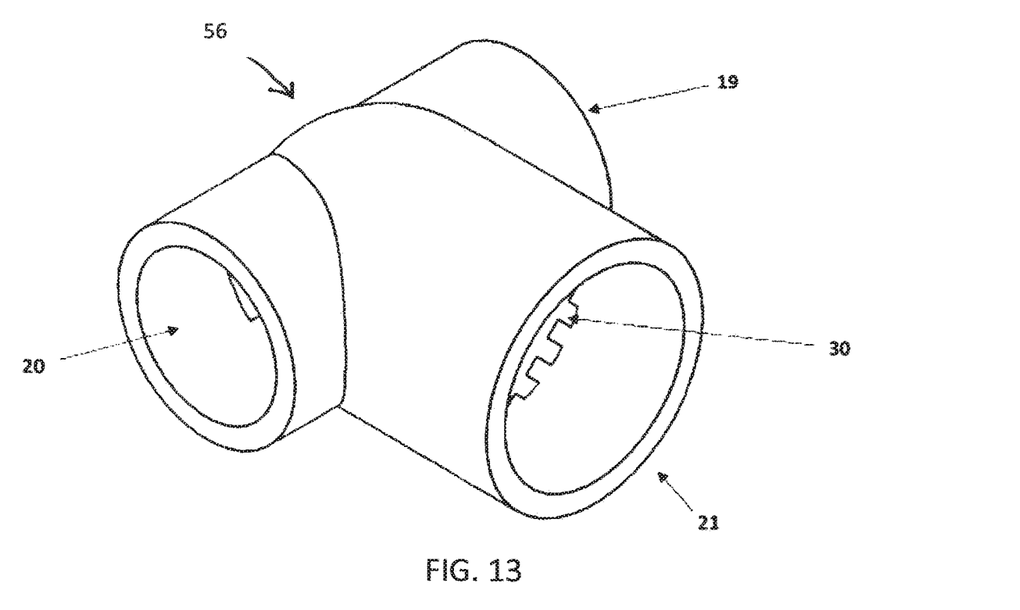
FIG. 13 is a perspective view of the T-shaped connector piece of the valve body, with a protective filter and two-way valve that connects the two manifold air passageways of the valve body to the mask shown in FIG. 19.
Figure 14:
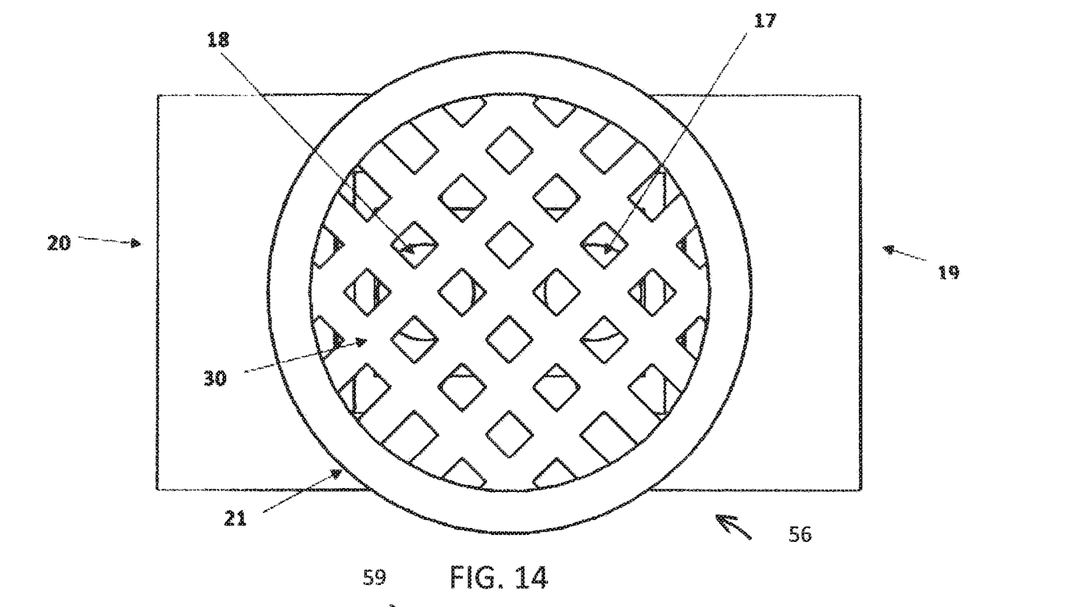
FIG. 14 is a bottom view of the T-connector piece of the valve body that connects to the mask shown in FIG. 19 so that the protective filter can be seen.

FIGS. 6 and 11 depict the air passageways 11 and 12 of the manifolds 51 and 52 of the valve body 50, through which each breath passes as is travels to the patient. The exterior of the manifolds 51 and 52 can be printed with indicia such as helpful information or instructions, to serve as a reminder to lifesavers of certain fundamental information that can sometimes be forgotten in an emergent situation. FIGS. 13-17 depict the efferent T-shaped connector piece 56 which serves as the joining point at which air from each of the manifolds 51 and 52 of the device reunite before traveling downward and into the mask 23 and ultimately to the patient.

The air inlets and air outlets on each of the respective manifolds 51 and 52 are offset on the respective manifolds 51 and 52. As best shown in FIG. 6, inflow port 9 is offset from the outflow port 26 with respect to a median or axis placed lengthwise through the center of the manifold 51, the median or axis generally in the direction of the pathway of airflow. Similarly, as shown in FIG. 11, inflow port 10 is offset with respect to outflow port 27 on the second manifold 52. Described another way, the respective inflow and outflow ports of each manifold are displaced or offset so that one is positioned nearer the top of the manifold, and one is positioned nearer the bottom of the manifold. This offset allows for the bag 1 and mask 23 to be stowed on top of one another and preferably within the space between the manifolds 51 and 52 when the bag-mask-valve is in the stowed configuration, as shown in FIG. 21.

The afferent T-shaped connector piece 58 is in fluid communication with inflow ports 9 and 10. The efferent T-shaped connector piece 56 is in fluid communication with outflow ports 26 and 27. In the preferred embodiments, the inflow and outflow ports are circular, allowing both the afferent T-shaped connector piece 58 and the efferent T-shaped connector piece 56 to be freely rotatable about the connections with the inflow and outflow ports. This ability to rotate about the ports allows the efferent T-shaped connector piece 56 and the afferent T-shaped connector piece 58 to rotate between the manifolds 51 and 52. This rotation also allows the bag 1 and mask 23 attached to the respective T-shaped connector pieces 56 and 58 to be stowed or located between the manifolds 51 and 52 in a first configuration, and located outside of between the manifolds 51 and 52 in a second configuration. In the preferred embodiment, the mask 23 and bag 1 may be inflated for use when removed from the stowed configuration. The connections between the manifolds 51 and 52 and the T-shaped connector pieces 56 and 58 may include mechanisms such as tabs and detents to allow the T-shaped connectors to be locked or resistant to movement when in the first or second configurations.

Figure 15:
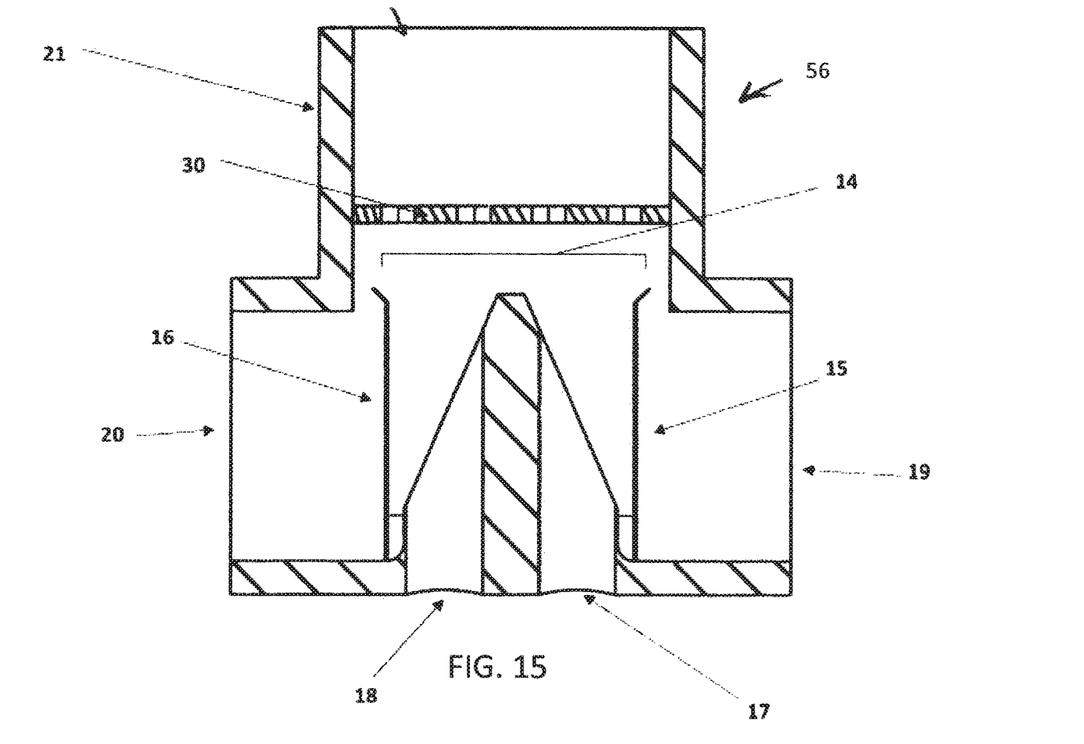
FIG. 15 is a cross-sectional view of the T-shaped connector piece that connects the two manifold air passageways of the valve body to the mask shown in FIG. 19 allowing for viewing of the valve with leaflets.
Figure 16:
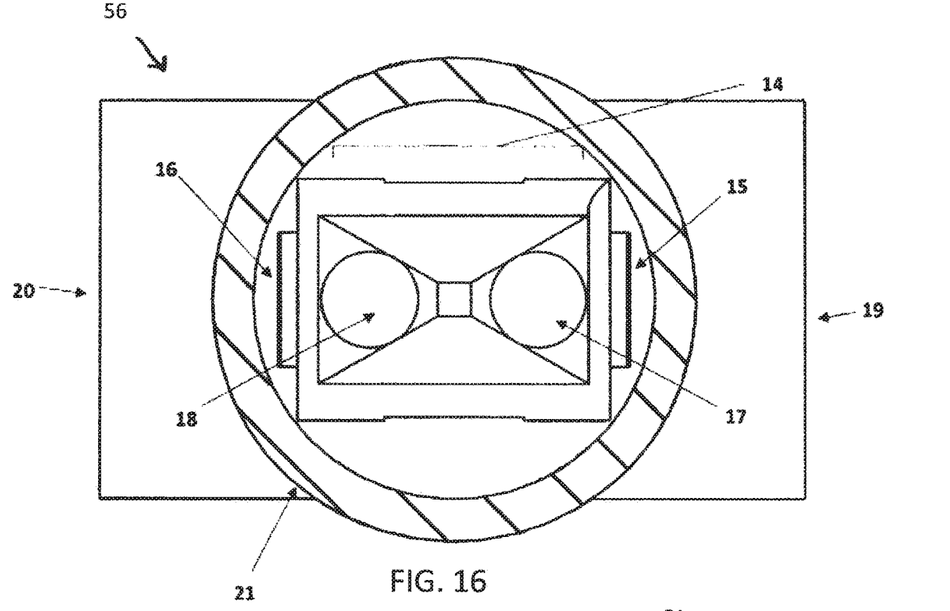
FIG. 16 is a bottom cross-sectional view of the T-connector piece, taken just above the level of the protective filter, showing the valve mechanism.
Figure 17:
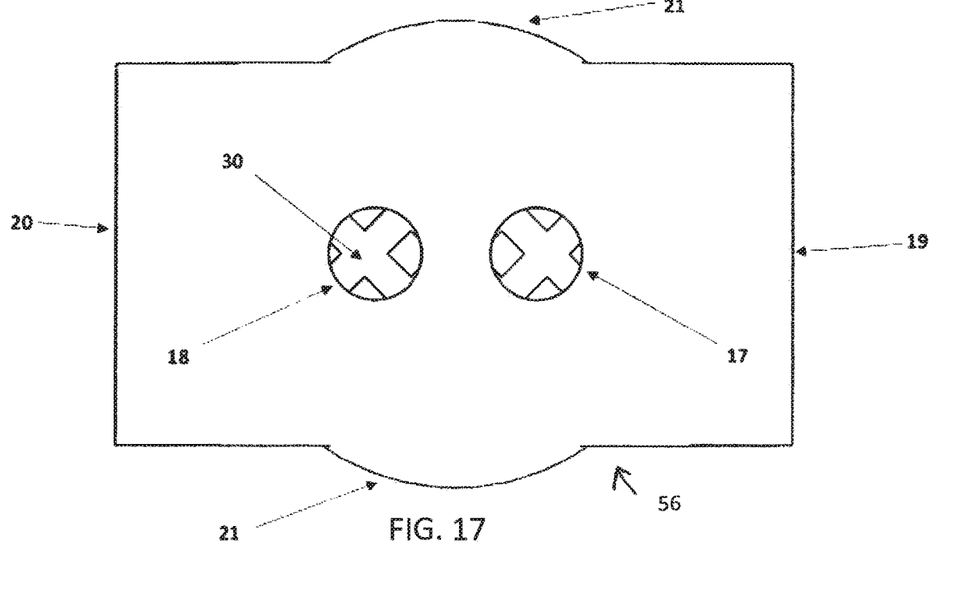
FIG. 17 is a top view of the T-connector piece used to connect to the mask shown in FIG. 19, showing the air escape points to the periphery used during patient exhalation.

As shown in FIG. 15, the efferent T-shaped connector piece 56 includes a valve 14 within the efferent T-connector piece 56, to allow exhaled air to be expelled into the periphery instead of into the air passageways 11 an 12 of the manifolds 51 and 52. The valve 14 preferably includes flexible leaflets or membranes 15 and 16 that move to a position to cover the vent holes 17 and 18 to ensure that the air is not expelled into the periphery but instead is directed downward and out of port 59 and into the mask 23 and to the patient during inhalation. These same leaflets 15 and 16 move to a position during exhalation to cover the air passageways 19 and 20 of the T-shaped connector piece to prevent the flow of exhaled air back into the manifolds 51 and 52 of the valve body 50, while instead guiding this air out and into the periphery by way of vent holes 17 and 18. In alternate embodiments, other valve structures may be used. For instance, the efferent T-connector piece 56 can include duck bill diaphragms to act as valves.

The neck 21 of the efferent T-shaped connector piece 56 which is designed to connect with the neck 22 of the mask 23, allowing the mask to be in fluid communication with the efferent t-shaped connector piece 56. This junction may be different from the junction between the bag 1 and the afferent T-connector 58 in that this union is designed to be readily disconnected as needed in order to connect the bag 1 and valve body 50 of the apparatus to a different device such as an endotracheal tube. Within the neck 21 of the efferent T-connector piece 56 is a protective filter 30 in place for the purpose of preventing transfer of particulate or other matter into the airway of the patient which would otherwise complicate resuscitation.

Figure 19:
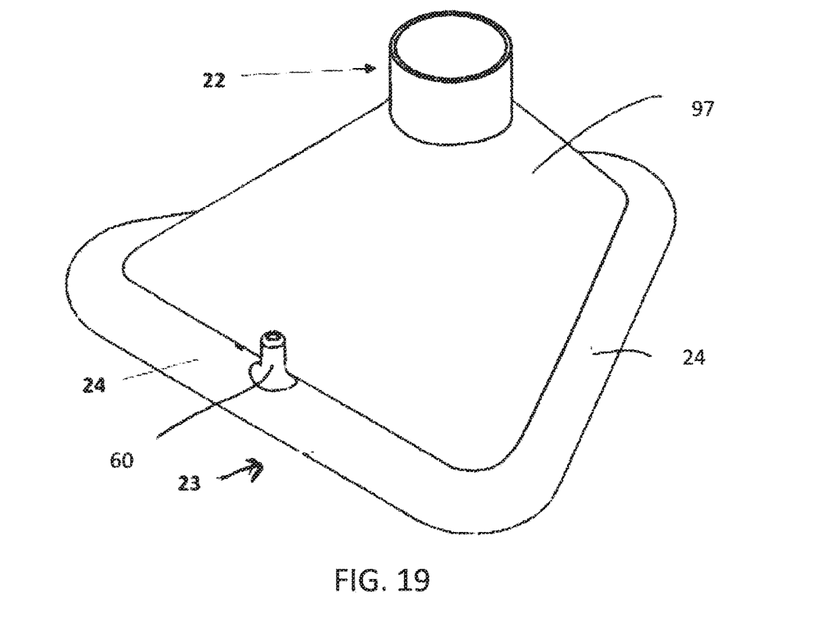
FIG. 19 is an isolated perspective view of the mask when it is expanded.
Figure 20:
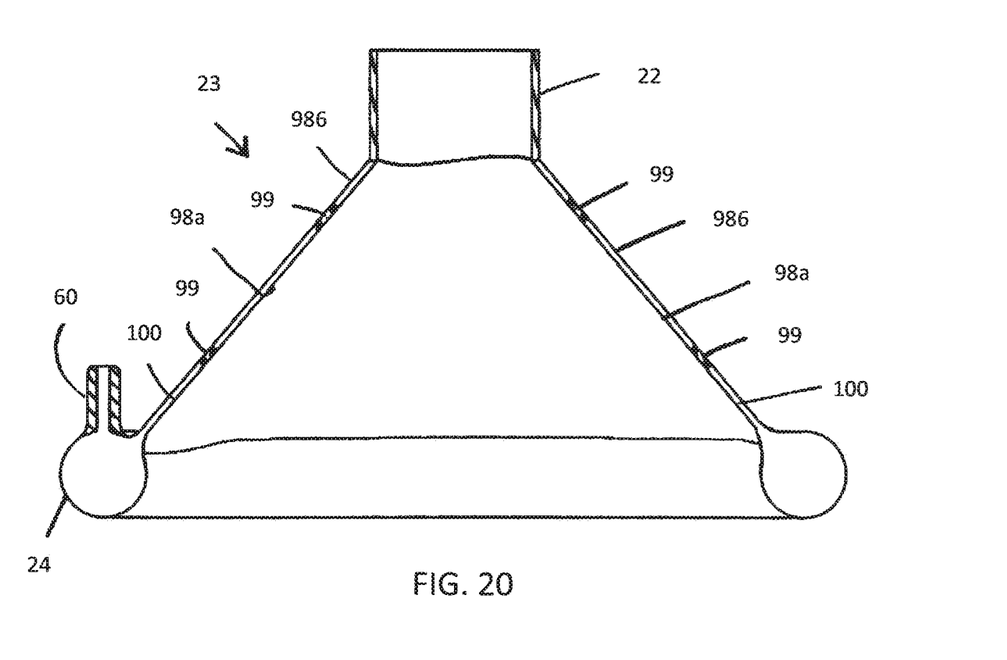
FIG. 20 is an isolated cross sectional view of the mask of FIG. 19 with its bilayer expanded to give it its deployed rigid shape, in this view one can identify both the inflatable bilayer of the mask as well as welding junctions where the two layers have been sealed together to provide stability between the two membranes of material that form the bilayer.

FIG. 19 depicts the mask 23 of the device which can be inflated or deflated as needed for product use or storage. The bottom of the mask 23 that will interact with the patient's face includes an inflatable perimeter 24 to create a cushioned interface and conform to the patient's mouth and nose area and ensure an adequate seal to resist air leakage. The inflation point or orifice 60 is used to inflate the mask 23, and is similar in function and use to as previously described for the bag 1. As shown in FIG. 20, the mask 23 also includes a neck 22 to connect to the efferent T-shaped connector 56. Between the inflatable perimeter 24 and the neck 22 is a wall 97. Similar to the bag 1, the wall 97 is a bilayer membrane that includes an inner layer 98a and an outer layer 98b, preferably connected by webs 99 at select locations. The airspace 100 between the inner layer 98a and the outer layer 98b may be in fluid communication with the inflatable perimeter 24. In other embodiments, the airspace 100 is not in fluid communication with the inflatable perimeter, and includes an inflation orifice.

FIG. 21 depicts the stowed configuration of the bag 1 and mask 23 folded into the space between the manifolds 51 and 52 or the interior portion 25 of the valve body 50 of the device. The placement of connection points on the manifolds to the T-shaped connectors 58 and 56 allow for turn-able components. Therefore, the compressed bag 1 (can be folded inwards to be on top of the compressed folded inwards mask 23. The general design of the device aims to minimize "pinch points" and sharp edges giving an overall rounded contoured design. These features, along with the device's ability to be manipulated to the user's needs, achieve optimal ergonomic function preventing injury, pain, or otherwise uncomfortable positioning for the user and the patient.

The foregoing disclosure of specific embodiments is intended to be illustrative of the broad concepts comprehended by the invention.

A respiratory assisting device comprising of an expandable bag which has a bilayer that can be inflated in order to give the bag a rigid and predetermined shape. The bag can then be compressed in order to displace inspiratory gas that is in the inner cavity and deliver it to the patient. The bag includes a one-way valve that passes through the bilayer allowing the inner cavity of the bag to fill with ambient air when the air within the cavity has been expended. The bag portion is connected to an air-tight hollow wall prism shape enclosure via a T-connector piece. This t-shaped connecting piece allows the air to pass through two manifold chambers that attach to another t-shaped connecting piece. One of the manifolds contains a pressure-release valve feature on the outer wall which vents air from the bag to the periphery if pressures within the system exceed a target pressure. The second t-connector piece has a two-way valve system within its walls to deliver the inspiratory air from the bag to inflate the patient's lungs while preventing exhaled air from the patient from entering back into the bag. Instead this expiratory air is vented into the periphery. Below the valve is a protective filter which serves as a safety mechanism to prevent the transmittance of any potentially dislodged components from within the device from being transferred down into the victim's airway. The air finally flows through a collapsible mask which can be inflated when needed to give it a rigid shape that conforms to the patient's face with the purpose of delivering and receiving rescue breaths. The t-shaped connector pieces are rotatable which permits the two inflatable portions of the device, the bag and the mask, to fold into the interior of section of the manifold enclosure for storage and transportation purposes.

We claim:

1. A respiratory assisting device including a bag, a valve body, and a mask, the bag being in fluid communication with the valve body, the valve body being in fluid communication with the mask, the valve body including a first connector having an inflow port in fluid communication with the bag, and a first outflow port and a second outflow port, the first outflow port being in fluid communication with a first manifold, and the second outflow port being in fluid communication with a second manifold, the first manifold being in fluid communication with a second connector, and the second manifold being in fluid communication with the second connector, the second connector being in fluid communication with the mask, wherein the first connector rotates between the first and second manifolds.

2. The apparatus of claim 1, wherein the bag is located between the first and second manifolds when in a first position and not located between the first and second manifolds when in a second position.

3. The apparatus of claim 2, wherein the second connector rotates between the first and second manifolds.

4. The apparatus of claim 1, wherein the bag and mask are located in a space between the first and second manifolds when the bag and mask are in respective first positions, and the bag and mask are not between the manifolds when in respective second positions.

5. The apparatus of claim 1, further including a valve in the second connector, the valve including a first vent and a second vent, the first and second vent communicating with the periphery, the valve directing air received from the manifolds to the mask, and directing air received from the mask to the first and second vents and out to the periphery.

6. The apparatus of claim 1, wherein the second connector is a T-shaped connector, the T-shaped connector including a first port in communication with the first manifold, a second port in communication with the second manifold, and a third port in communication with the mask, the first and second ports being axially aligned, the T-shaped connector further including a first vent and a second vent to communicate with the periphery, a first membrane to cover the first vent when air is received into the first port from the first manifold and a second membrane to cover the second vent when air is received into the second port from the second manifold, the first membrane moving to cover the first port and the second membrane moving to cover the second port when air is received in the third port from the mask.

7. A respiratory assisting device including a bag, a valve body, and a mask, the bag being in fluid communication with the valve body, the valve body being in fluid communication with the mask, the mask including a wall constructed of a bilayer material, the valve body including a first connector having an inflow port in fluid communication with the bag, and a first outflow port and a second outflow port, the first outflow port being in fluid communication with a first manifold, and the second outflow port being in fluid communication with a second manifold, the first manifold being in fluid communication with a second connector, and the second manifold being in fluid communication with the second connector, the second connector being in fluid communication with the mask.

8. The apparatus of claim 7, wherein the mask includes an inflatable perimeter, the inflatable perimeter in fluid communication with an airspace located between layers of the bilayer material forming the wall.

9. The apparatus of claim 7, wherein the second connector includes a filter.

* * * * *